United States Patent [19]

Strenk

[11] Patent Number: 5,144,236
[45] Date of Patent: Sep. 1, 1992

US005144236A

[54] METHOD AND APPARATUS FOR R.F. TOMOGRAPHY

[75] Inventor: Lawrence M. Strenk, Middleburg Hts., Ohio

[73] Assignee: Strenk Scientific Consultants, Inc., Middleburg Heights, Ohio

[21] Appl. No.: 570,204

[22] Filed: Aug. 17, 1990

[51] Int. Cl.⁵ .......................................... G01R 33/20
[52] U.S. Cl. ................................................ 324/309
[58] Field of Search ............... 324/300, 307, 309, 318, 324/322

[56] References Cited

U.S. PATENT DOCUMENTS

| | | | |
|---|---|---|---|
| 3,932,805 | 1/1976 | Abe et al. | 324/309 |
| 4,135,131 | 1/1979 | Larsen et al. | |
| 4,247,815 | 1/1981 | Larsen et al. | |
| 4,271,389 | 6/1981 | Jacobi et al. | |
| 4,425,547 | 1/1984 | Sugimoto | 324/309 |
| 4,552,151 | 11/1985 | Bolomey et al. | |
| 4,641,659 | 2/1987 | Sepponen | |
| 4,695,800 | 9/1987 | Kramer et al. | 324/309 |
| 4,805,627 | 2/1989 | Klingenbeck et al. | |
| 4,984,573 | 1/1991 | Leunbach | 324/309 |

OTHER PUBLICATIONS

David J. Griffiths, *Introduction to Electrodynamics*, 1989, pp. 369-371.
Edward E. Christensen, M.D., Thomas S. Curry, III, M.D., James E. Dowdey, Ph.D., *An Introduction to physics of Diagnositc Radiology*, pp. 329-360, 1978.
Malcolm Slaney, Avinash C. Kak, Lawrence E. Larsen, *Limitations of Imaging with First-Order Diffraction Tomography*, Oct. 12, 1984, pp. 860-873.
Itsuo Yamura, *Measurements of 1.8-2.7-GHz Microwave Attenuation in the Human Torso*, Apr. 14, 1976, revised Dec. 17, 1976, pp. 707-710.
Curtis C. Johnson, Arthur W. Guy, *Nonionizing Electromagnetic Wave Effects in Biological Materials and Systems*, Feb. 24, 1972, revised Mar. 20, 1972, pp. 692-718.

*Primary Examiner*—Michael J. Tokar
*Attorney, Agent, or Firm*—Pearne, Gordon, McCoy & Granger

[57] ABSTRACT

A coil is used to transmit r.f. energy pulses through an object to be imaged. The pulses are transmitted at a plurality of directions coplanar with the image plane. A receiving coil picks up the transmitted r.f. energy. The received energy is converted to values corresponding to the amount of absorption of the energy by the object at a particular direction. By using r.f. frequencies having a wavelength less than the greatest dimension of the object, reflection, refraction and diffraction effects are minimized. The use of coils for transmitting and receiving allows propagating the energy with reasonable sized devices. Because tomographic techniques are used for image creation, the large wavelength does not seriously impact resolution.

14 Claims, 3 Drawing Sheets the  # METHOD AND APPARATUS FOR R.F. TOMOGRAPHY

BACKGROUND OF THE INVENTION

The present invention relates to a method and apparatus for forming a tomographic image of an object based on its absorption of a long wavelength electromagnetic field.

The absorption of electromagnetic waves has been used for over a century in the field of medical diagnosis. In particular, x-rays have been used. At the high energy and frequency of x-rays, the difference in absorption between high density tissue, such as bone, and low density tissue, such as fat, is used for contrast in the images produced.

Unfortunately, the contrast between low density materials, such as fat and water, is difficult to measure with x-rays. Furthermore, the high energy of the waves causes damaging ionization in the body.

Research in lower energy wave absorption has been limited to microwave frequencies (generally defined to be greater than 1 GHz). Attempts have been made to use microwaves to produce tomographs, computed axial tomographs, and fluoroscopic images (see U.S. Pat. Nos. 4,805,627; 4,641,659; 4,552,151; 4,271,389; 4,247,815; and 4,135,131).

The major problem with microwave image formation is that the object to be scanned is much larger than the microwave wavelength. Consequently, the conducting objects in the body act as antennae to the waves and produce multiple reflections, diffractions and refractions (see "Nonionizing Electromagnetic Wave Effects in Biological Materials and Subsystems," Johnson et al., Proceedings of IEEE, Vol. 60, No. 6, 1972, pages 692–718 and "Measurements of 1.8–2.7-GHz Microwave Attenuation in the Human Torso," Yamaura, IEEE Transactions on Microwave Theory and Techniques, Vol. MTT-25, No. 8, 1977, pages 707–710).

As a result, the decrease in intensity of the wave cannot be attributed to one source, but to many apparent sources. This can distort the image (see "Limitations of Imaging with First-Order Diffraction Tomography," Slaney et al., IEEE Transactions on Microwave Theory and Techniques, Vol. MTT-32, No. 8, 1984, pages 860–874).

In addition, because of the high proportion of the microwave energy absorbed, excessive heating and hot spots due to standing waves between conducting areas can result. If this effect is reduced by reducing the intensity or the duty-cycle, the scan time must be extended, thus increasing motion artifacts.

One approach to avoiding these problems has been the use of nuclear magnetic resonance imaging. NMR uses a large static magnetic field to induce a net magnetic moment in each voxel of the object being imaged. A magnetic field oscillating in the r.f.-range flips these magnetic moments perpendicular to the main field. The dipole moment then precesses about the main field axis at a rate proportional to the product of the gyromagnetic ratio and the main field. Spatial localization is achieved through the use of external magnetic field gradients.

Unlike x-ray imaging or r.f. absorption imaging, the precessing of the magnetic moments about the main field axis is the mechanism that provides the output signals in NMR. This mechanism provides contrast between various soft tissues and the object being imaged absorbs very little energy. Unfortunately, the generation of the main magnetic field requires the use of large and expensive electromagnets. These electromagnets represent a substantial portion of the cost and complexity of NMR systems.

SUMMARY OF THE INVENTION

The present invention includes a method for imaging an object. Electromagnetic energy is transmitted through the object at each of a plurality of directions in a plane through the object.

In the preferred embodiment, the electromagnetic energy has a wavelength greater than the greatest dimension of the object within the plane, but somewhat shorter wavelengths may be used. In general, frequencies less than 1 GHz are desirable (0.3 meter wavelength). By using relatively long wavelength energy, multiple scattering within the object is minimized, as is absorption of the imaging energy by the object.

The transmitted energy is received for each of the directions and a value is measured that is representative of the absorption by the object for that direction.

These absorption values are then transformed into an image of the object within the plane. This transformation may be accomplished, for example, by back projection or by solving a system of linear equations of the values.

The invention also includes an apparatus for providing an image of the portion of an object lying in a plane through the object. The apparatus includes an electromagnetic energy source, a transmitting coil adapted to transmit energy from the source a transmitting coil adapted to transmit energy from the source through the object at each of a plurality of directions in the plane, a receiving coil adapted to receive the energy at each of the directions, means for measuring a value representative of the absorption by the object of the transmitted energy at each of the directions, and means for transforming the absorption values into an image of the object within the plane.

The use of coils to transmit and receive the electromagnetic energy avoids the problems of trying to propagate and detect the electromagnetic energy using the typical antenna approach. At the wavelengths involved, a typical dipole antenna would be too large.

It should be understood that while the image is referred to as lying within a plane, it is really a section or slice of the object about the plane that is imaged. A further advantage of the use of transmitting and receiving coils is that the dimensions of the coils can be readily manipulated to control the thickness of the slice of the object that is imaged.

In one embodiment of the invention, means are provided to translate the coils within the plane transversely to each of the directions. This allows pulses to be sent at various transverse displacements before orienting the coils for another of the plurality of directions.

In another embodiment of the invention, an array of the transmitting coils and an array of the receiving coils are located within the plane. The receiving coils are adapted to receive pulses from respective transmitting coils.

In another embodiment of the invention, a plurality of the transmitting and receiving coils are located in the plane and encircling the object. Each of these coils are selectably operable as either a receiving coil or a transmitting coil.

The present invention can provide good soft tissue image contrast without the expense and complexity of large static field electromagnets. It is able to generate high resolution images without the use of short wavelength electromagnetic energy, particularly without ionizing radiation.

DESCRIPTION OF THE PREFERRED EMBODIMENTS

Figure 1:
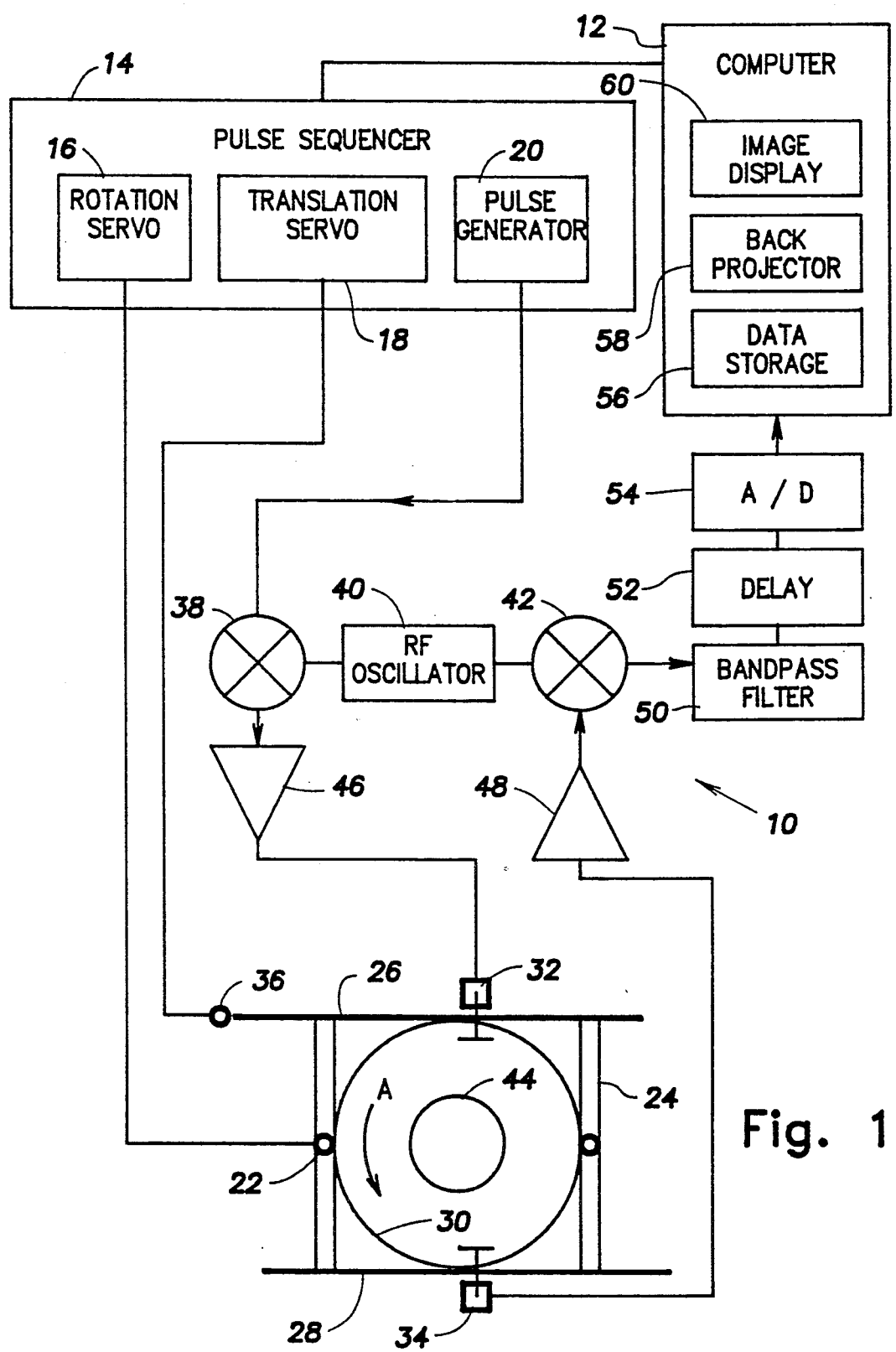
FIG. 1 is a block diagram of an apparatus according to the invention.

Referring to FIG. 1, an apparatus 10 according to the invention is shown. A computer 12 provides control of a pulse sequencer 14. The pulse sequencer 14 includes a rotation servo control 16, a translation servo control 18 and a pulse generator 20.

The rotation servo control 16 controls a servomotor 22 attached to a frame 24 that includes a transmitter translation track 26 and a receiver translation track 28 arranged parallel to each other. The servomotor 22 is configured to rotate the frame 24 about a ring 30 in direction A under the control of the rotation servo control 16; the tracks 26, 28 being tangent to the cylinder of rotation.

A transmitting coil 32 is attached to the track 26 and a receiving coil 34 is attached to the track 28 in a manner such that a servomotor 36 can synchronously translate the transmitting coil 32 and the receiving coil 34 along the track 26 and the track 28, respectively. This translation is controlled by the translation servo control 18. The coils 32, 34 rotate with the frame 24 about the ring 30.

The pulse generator 20 provides a pulse waveform to a power combiner or modulator 38. An r.f. oscillator 40 provides a radio frequency signal to the modulator 38 and a demodulator 42. The frequency of the r.f. signal may, for example, be less than 1 GHz. In the preferred embodiment, the wavelength of the r.f. signal is greater than the largest dimension of the object 44 in the plane determined by the rotation of the coils 32, 34 about the ring 30.

The modulator 38 provides an r.f. pulse train having an envelope corresponding to the pulse train from the pulse generator 20 and the r.f. frequency of the r.f. oscillator 40. This r.f. pulse train is applied to a power amplifier 46, which in turn provides a signal to the transmitting coil 32, where it is propagated toward the receiving coil 34.

The receiving coil 34 receives a portion of this propagated electromagnetic energy signal and applies it to an amplifier 48. The amplifier 48 provides an amplified version of the received signal from the coil 34 to the demodulator 42.

The demodulator provides an output signal to a bandpass filter 50 which passes the baseband portion of the signal from the demodulator 42 to a variable delay 52. This baseband signal corresponds to the transmitted r.f. pulse train as absorbed by the object 44.

The delay 52 is adjustable such that either the center of the attenuated envelope or the corresponding phase shift of the pulse train may be sampled by an analog-to-digital converter 54.

The attenuation of the envelope provides good results for low conductivity media (such as biological tissue). Either the phase or the attenuation provides good results for high conductivity media.

The digital output of the converter 54 is stored in a data storage 56 associated with the computer 12. This data is manipulated by a back projection algorithm 58 within the computer 12 to provide an image on an image display 60.

In operation, a pulse from the pulse generator 20 causes an r.f. pulse to be applied to the coil 32. The coil 32 produces an r.f. oscillating magnetic field $B_0$ for each pulse from the pulse generator 20. As the magnetic field $B_0$ propagates through the object 44, it produces, by Faraday's Law, a circular oscillating electric field E. Then by Ohm's Law, as this electric field oscillates, a circular current density $J = \sigma E$ flows in the first incremental volume or voxel of the object that the field encounters, where the conductivity of this voxel is $\sigma$.

The current density J produces its own oscillating magnetic field $B_1$, which by Lenz's Law, opposes the applied field $B_0$. The magnetic field at the next voxel of the object 44 is reduced from $B_0$ by the amount $B_1$. Repeated application of this process through the entire medium reduces the r.f. magnetic field B(r) at the coil 34 by $B(r)/(B_0 f(r)) = e^{-\alpha}$, where r is the distance of the coil 34 from the coil 32, f(r) is the drop off of the field B(r) in a non-conducting medium and $\alpha$ is the integrated absorption coefficient, given by $\alpha = \Sigma k(r) \Delta r$, where k is the complex wave number and $\Delta r$ is the length of a voxel (see "Introduction to Electrodynamics," Griffiths, Prentice Hall, New Jersey 1989).

The reduced r.f. magnetic field B(r) is picked up by the coil 34. This results in a value representative of the amount of absorption (which consists of both an attenuation and phase component) by the object 44 of the transmitted r.f. electromagnetic energy being stored in the data storage 56, along with the position of the coils 32, 34 on the tracks 26, 28, respectively, and the angular position or angle of the frame 24 about the axis of the ring 30.

The coils 32, 34 are repeatedly moved along the tracks 26, 28, respectively, to provide a complete projection of the object 44. After each movement, a new pulse is transmitted by the coil 32 resulting in another set of values being stored in the data storage 56.

After data from a projection are stored, the frame 24 is rotated a small angle $\Delta \Phi$ about the axis of the ring 30 and the above process repeated. In this way a series of projections $P(\Phi)$ of the object 44 are created, each being angularly dependent. Typically, this process will be continued until the frame 24 has been rotated through 180°.

Once this data is amassed in the data storage 56, the projections are reconstructed into an image I(x,y) for display on the image display 60 by the back projector algorithm 58 ($I(x,y) = \Sigma P(\Phi) \Delta \Phi$), where x and y are the position of each pixel (see "An Introduction to the Physics of Diagnostic Radiology," Christensen et al., Lea & Febiger, 1978, pages 343-44).

When the object 44 is biological tissue, the difference in contrast in the image is determined by the differences in conductivity $\sigma$ between the tissue of high water content and that of tissue of low water content. The slice thickness is determined by the diameter of the receiving coil 34. Adjacent slices, and hence 3-dimensional images, can be achieved by moving the object 44 into or out of the plane of FIG. 1 and repeating the process.

Figure 2:
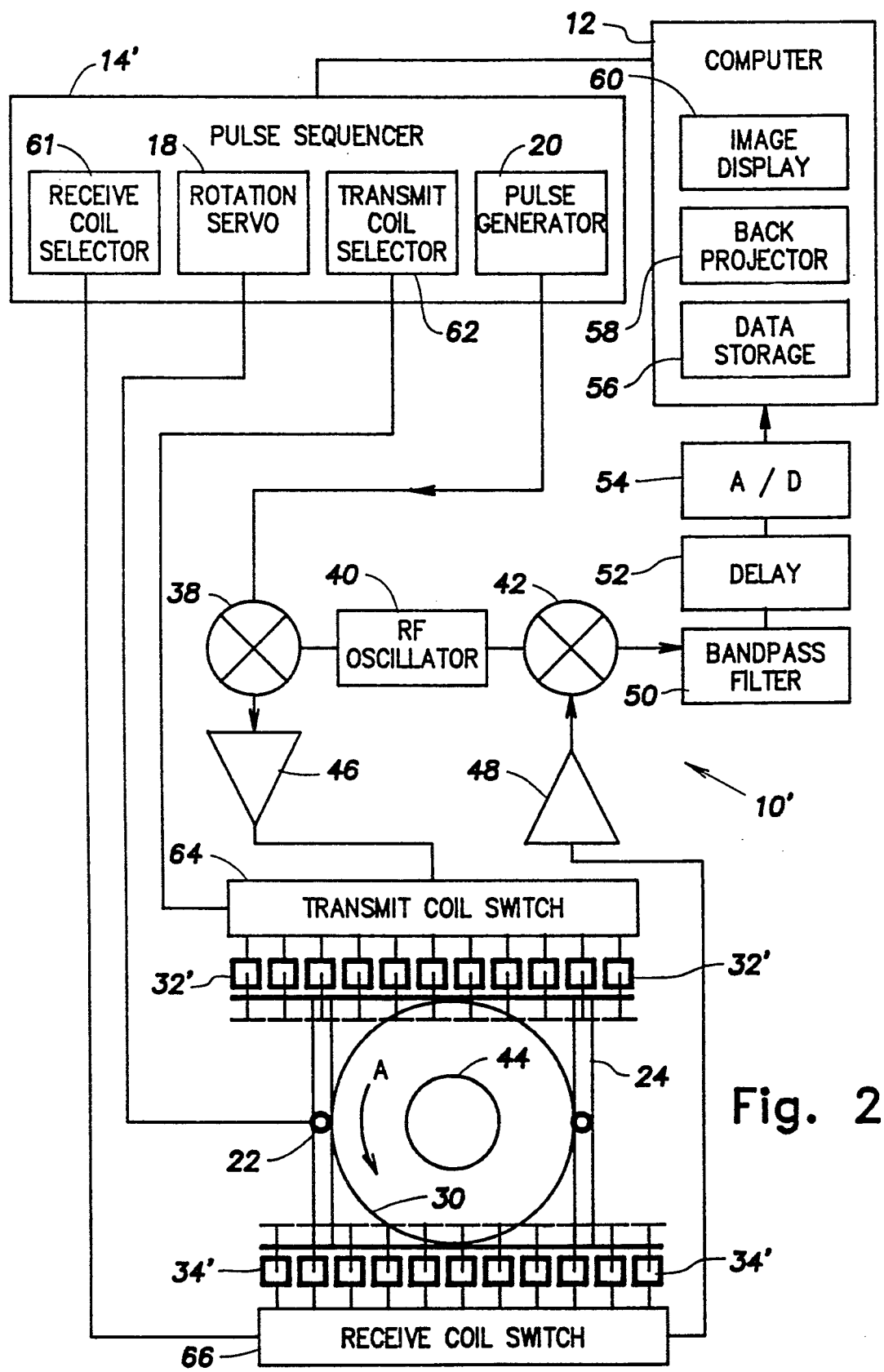
FIG. 2 is a block diagram of an additional embodiment of the invention.

FIG. 2 shows an another embodiment of the invention. Instead of translating the coils 32, 34 along the tracks 26, 28, respectively, as in the embodiment of FIG. 1, linear arrays of transmitting coils 32' and receiving coils 34' are provided along opposite sides of the frame 24. To provide the necessary projection of the object 44, the pulse sequencer 14' is provided with a receive coil selector 61 and a transmit coil selector 62. The transmit coil selector 62 controls a transmit coil switch 64 which determines which coil 32' in the array is connected to the power amplifier 46. Similarly, the receive coil selector 61 controls a receive coil switch 66 which determines which coil 34' in the array is connected to the amplifier 48. By switching to successive oppositely located pairs of coils 32', 34', the same effect as translating the coils 32, 34 transversely to the angle of the frame 24 can be achieved.

Eliminating the translational motion of the transmitting and receiving coils results in higher resolution and improved accuracy of the projection acquired in a shorter period of time.

Figure 3:
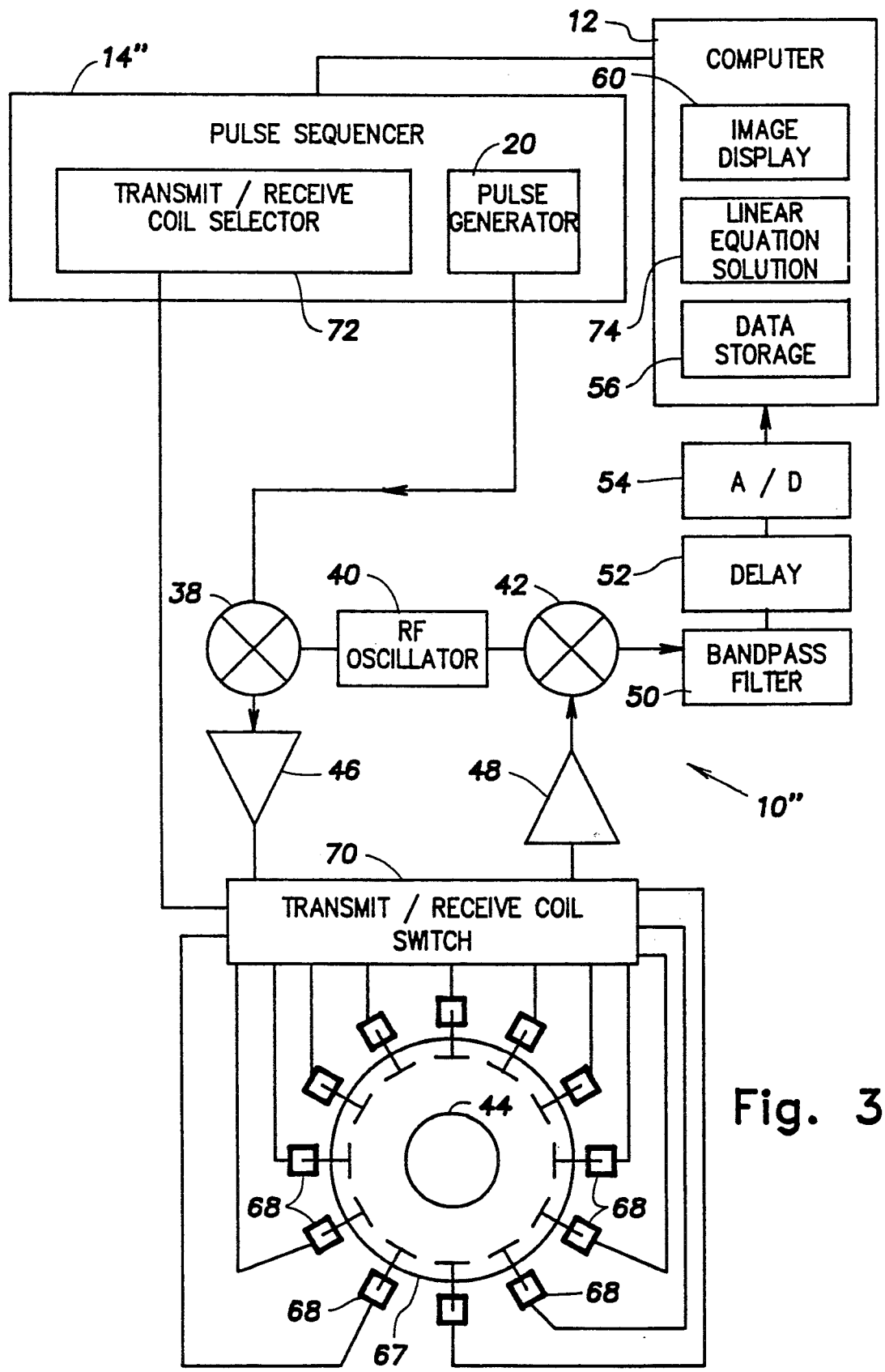
FIG. 3 is a block diagram of another additional embodiment of the invention.

FIG. 3 shows an additional another embodiment of the invention. In this embodiment, a ring 67 is provided with a circular array of combination transmit/receive coils 68. A transmit/receive coil switch 70 determines which one of the coils 68 is connected to the power amplifier 46 and which is connected to the amplifier 48. The transmit/receive coil switch is controlled by a transmit/receive coil selector 72 in the pulse sequencer 14''.

In operation, the coils are switched to provide the desired angular dependence of the projection $P(\Phi)$, taking into account the correction for the curvature of the projection.

Eliminating both the translational and rotational motion of the coils improves acquisition speed and the positional accuracy of the projections.

In addition, the embodiment of FIG. 3 substitutes a linear equation solving algorithm 74 for the back projector algorithm 58. In this case the image is produced by solving the system of linear equations determined from the integrated absorption coefficient $\alpha$ and the formula for the magnetic field $B(r)$ for each of the projections $P(\Phi)$. This results in an image $I(x,y) = k(x,y)$ where $k(x,y)$ is a function of the conductivity $\sigma$ (see "Introduction to Electrodynamics," Griffiths, Prentice Hall, New Jersey 1989). This method of image reconstruction can be applied to the embodiments of FIGS. 1 and 2 as well.

In all of the embodiments, to acquire images at different viewing angles, the object and transmit and receive coil combinations can be rotated relative to each other. In addition, multiple rings or planar arrays of transmitting coils and receiving coils can be combined to produce multiple and variable viewing angle images.

It should be noted that the invention may also be practiced with non-pulsed r.f. energy. This increases the likelihood of affecting the object being imaged and requires circuitry adapted to handle a greater duty cycle.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A method for imaging a radio frequency energy absorbing object, said method comprising:
    transmitting radio frequency energy through said object in a first direction, a portion of said radio frequency energy being absorbed by said object and a portion being transmitted through said object;
    receiving said transmitted portion of said radio frequency energy in said first direction;
    converting said received radio frequency energy into a first absorption quantity representative of the portion of said radio frequency energy absorbed by said object in said first direction;
    repeating said transmitting, receiving and converting steps for a plurality of additional directions, each of said directions lying in a plane and each repetition providing an additional absorption quantity, said object having dimensions within said plane, one of said dimensions being a greatest dimension; and
    transforming said absorption quantities into an image of the object within said plane, said radio frequency energy having a wavelength greater than said greatest dimension.

2. A method according to claim 1, wherein said transforming is by back projecting said absorption quantities.

3. A method according to claim 1, wherein said transforming is by solving a system of linear equations of said absorption quantities.

4. A method according to claim 1, wherein said radio frequency energy has a frequency of less than 1 GHz.

5. An apparatus for imaging a radio frequency energy absorbing object, said apparatus comprising:
    means for transmitting radio frequency energy through said object in a first direction, a portion of said radio frequency energy being absorbed by said object and a portion being transmitted through said object;
    means for receiving said transmitted portion of said radio frequency energy in said first direction;
    means for converting said received radio frequency energy into a first absorption quantity representative of the portion of said radio frequency energy absorbed by said object in said first direction;
    means for controlling said transmitting, receiving and converting means to provide an additional absorption quantity for each of a plurality of additional direction, said directions lying in a plane, said object having dimensions within said plane, one of said dimensions being a greatest dimension; and
    means for transforming said absorption quantities into an image of the object within said plane, said radio frequency energy having a wavelength greater than said greatest dimension.

6. An apparatus according to claim 5, wherein said transforming means is adapted to back project said absorption quantities to obtain said image.

7. An apparatus according to claim 5, wherein said transforming means is adapted to solve a system of linear equations of said absorption quantities to obtain said image.

8. An apparatus according to claim 5, wherein said radio frequency energy has a frequency of less than 1 GHz.

9. An apparatus for providing an image of a radio frequency energy absorbing object within a plane through the object, said apparatus comprising:
- a radio frequency energy source;
- a transmitting coil adapted to transmit radio frequency energy from said source through said object at each of a plurality of directions in said plane;
- a receiving coil adapted to receive said radio frequency energy at each of said directions;
- means for measuring a quantity representative of the absorption by said object of said transmitted radio frequency energy at each of said directions; and
- means for transforming said quantities into an image of the object within said plane.

10. An apparatus according to claim 9, wherein said transforming means is adapted to back project said quantities to obtain said image.

11. An apparatus according to claim 9, wherein said transforming means is adapted to solve a system of linear equations of said quantities to obtain said iamge.

12. An apparatus according to claim 9, further comprising means to translate said coils within said plane transversely to each said direction.

13. An apparatus according to claim 9, further comprising:
- an array of said transmitting coils located within said plane; and
- an array of said receiving coils located within said plane, said array of receiving coils being adapted to receive pulses from respective transmitting coils.

14. An apparatus according to claim 9, further comprising a plurality of said transmitting and receiving coils located in said plane and encircling said object, each said coil being selectably operable as either a receiving coil or a transmitting coil.

* * * * *

UNITED STATES PATENT AND TRADEMARK OFFICE
CERTIFICATE OF CORRECTION

PATENT NO. : 5,144,236

DATED : September 1, 1992

INVENTOR(S) : Lawrence M. Strenk

It is certified that error appears in the above-identified patent and that said Letters Patent is hereby corrected as shown below:

Title page, item [56], "Other Publications" 2nd col. line 2, "physics" should be --Physics--.

Title page, item [56], Other Publications" 2nd col. line 5, "Oct. 12, 1984," should be --Oct. 12, 1983,--.

Title page, item [56], "Other Publications", 2nd col. line 5, before "pp. 860-873." insert --revised Mar. 9, 1984,--.

Column 2, lines 33-34, delete "a transmitting coil adapted to transmit energy from the source".

Col. 6, line 51, "direction" should be --directions--.

Signed and Sealed this

Fourteenth Day of September, 1993

Attest:

BRUCE LEHMAN

*Attesting Officer*  *Commissioner of Patents and Trademarks*